US009851355B2

(12) United States Patent
Daniely et al.

(10) Patent No.: US 9,851,355 B2
(45) Date of Patent: Dec. 26, 2017

(54) METHODS OF DETERMINING RESPONSE TO THERAPY

(71) Applicant: Alcobra Ltd., Tel Aviv (IL)

(72) Inventors: Yaron Daniely, Tel Aviv (IL); Jonathan Rubin, Newtown Square, PA (US); Johanna Schumann, Modi'in (IL)

(73) Assignee: Alcobra Ltd., Tel Aviv (IL)

( * ) Notice: Subject to any disclaimer, the term of this patent is extended or adjusted under 35 U.S.C. 154(b) by 0 days.

(21) Appl. No.: 14/917,171

(22) PCT Filed: Sep. 9, 2014

(86) PCT No.: PCT/US2014/054816

§ 371 (c)(1), (2) Date: Mar. 7, 2016

(87) PCT Pub. No.: WO2015/035402

PCT Pub. Date: Mar. 12, 2015

(65) Prior Publication Data

US 2016/0216265 A1 Jul. 28, 2016

Related U.S. Application Data

(63) Continuation of application No. 14/038,258, filed on Sep. 26, 2013, now abandoned.

(60) Provisional application No. 61/875,384, filed on Sep. 9, 2013, provisional application No. 61/991,351, filed on May 9, 2014.

(51) Int. Cl.

| | |
|---|---|
| ***G01N 33/573*** | (2006.01) |
| ***A61K 31/4425*** | (2006.01) |
| ***A61K 31/4015*** | (2006.01) |
| ***A61K 9/00*** | (2006.01) |
| ***A61K 31/4439*** | (2006.01) |

(52) U.S. Cl.

CPC ......... *G01N 33/573* (2013.01); *A61K 9/0053* (2013.01); *A61K 31/4015* (2013.01); *A61K 31/4425* (2013.01); *A61K 31/4439* (2013.01); *G01N 2333/91205* (2013.01); *G01N 2440/14* (2013.01); *G01N 2800/30* (2013.01); *G01N 2800/52* (2013.01)

(58) Field of Classification Search

None

See application file for complete search history.

(56) References Cited

U.S. PATENT DOCUMENTS

| | | | |
|---|---|---|---|
| 4,313,952 | A | 2/1982 | Baldacci |
| 8,476,304 | B2 | 7/2013 | Megiddo et al. |
| 8,710,067 | B2 | 4/2014 | Yamin et al. |
| 2010/0256198 | A1 | 10/2010 | Megiddo et al. |
| 2012/0264781 | A1 | 10/2012 | Yamin et al. |
| 2015/0073023 | A1 | 3/2015 | Daniely et al. |
| 2015/0335629 | A1 | 11/2015 | Daniely et al. |
| 2016/0193199 | A1 | 7/2016 | Daniely et al. |

FOREIGN PATENT DOCUMENTS

| | | | |
|---|---|---|---|
| WO | WO 02/43507 | A2 | 6/2002 |
| WO | WO 2009/004629 | A2 | 1/2009 |
| WO | WO 2010/150261 | A1 | 12/2010 |
| WO | WO 2015/033224 | A2 | 3/2015 |
| WO | WO 2015/035402 | A1 | 3/2015 |

OTHER PUBLICATIONS

Liu et al., Lithium reverses increased rates of cerebral protein synthesis in a mouse model of fragile X syndrome, Mar. 2012, Neurobiology of Disease 45(3):1145-1152.*

"Attention Deficit Hyperactivity Disorder (ADHD)" California State University, Accessibility Resource Center, printed Apr. 30, 2014 (2 pages).

"FDA Grants Orphan Status to Metadoxine in Fragile X Syndrome" Globenewswire.com News Release, Dec. 18, 2013 (4 pages).

Addolorato, G., et al., "Metadoxine in the treatment of acute and chronic alcoholism: a review." Int. J. Immunopathol. Pharmacol. (2003); 16:207-214.

Cook, N.R., "Use and misuse of the receiver operating characteristic curve in risk prediction." Circulation (2007); 115.7: 928-935.

D'Agostino Sr., et al., "Validation of the Framingham coronary heart disease prediction scores: results of a multiple ethnic groups investigation." JAMA (2001); 286.2: 180-187.

Ethell and Yamaguchi, "Cell surface heparan sulfate proteoglycan syndecan-2 induces the maturation of dendritic spines in rat hippocampal neurons." The Journal of Cell Biology (1999); 144.3: 575-586.

Ethell et al., "EphB/syndecan-2 signaling in dendritic spine morphogenesis." Neuron (2001); 31.6: 1001-1013.

Fraxa Research Foundation, http://www .fraxa.org/neuren-pharmaceuticals-trial-new-drug-autismfragilex/, accessed Jun. 30, 2014, 3 pages.

Henkemeyer et al., "Multiple EphB receptor tyrosine kinases shape dendritic spines in the hippocampus." The Journal of Cell Biology (2003); 163.6: 1313-1326.

Hoeffer et al., "Inhibition of the interactions between eukaryotic initiation factors 4E and 4G impairs long-term associative memory consolidation but not reconsolidation." PNAS (2011); 108(8): 3383-3388.

Holzman et al. "Teva and Alcobra Announce Phase II Trial of Novel, Non-Stimulant MG01CI for ADHD Meets Primary Endpoint." Drugs.com, http://www.drugs.com/clinical_trials/teva-alcobra-announce-phase-ii-trial-novel-non-stimulant-mg01ci-adhd-meets-primary-endpoint-12311.html, published Sep. 2011); accessed Feb. 4, 2014, 8 pages.

(Continued)

*Primary Examiner* — John Ulm

(74) *Attorney, Agent, or Firm* — Cooley LLP; Ivor Elrifi; Cynthia Kozakiewicz

(57) ABSTRACT

The present invention relates generally to methods of determining the response to metadoxine therapy for the treatment of Fragile X Syndrome and other cognitive disorders. The invention also relates to identifying individuals that will be responsive to metadoxine therapy.

7 Claims, 16 Drawing Sheets

(56) References Cited

OTHER PUBLICATIONS

Klann and Dever, "Biochemical mechanisms for translational regulation in synaptic plasticity." Nature Reviews Neuroscience (2004); 5.12: 931-942.

Langer, "New Methods of Drug Delivery," Science (1990); 249:(4976): 1527-1533.

Lopez Verrilli et al., "Angiotensin-(1-7) through AT2 receptors mediates tyrosine hydroxylase degradation via the ubiquitin-proteasome pathway." Journal of Neurochemistry (2009); 109.2: 326-335.

Lü, Yuan, et al., "Pharmacokinetics of Metadoxine for Injection After Repeated Doses in Healthy Volunteers," Chin. Med. J. (2007); 120(2):160-168.

Manor, I, et al. "A randomized, double-blind, placebo-controlled, multicenter study evaluating the efficacy, safety, and tolerability of extended-release metadoxine in adults with attention-deficit/hyperactivity disorder." The Journal of Clinical Psychiatry (2012); 73(12): 1517-1523.

McCracken et al., "Risperidone in children with autism and serious behavioral problems." N Engl J Med. (2002); 347(5): 314-321.

O'Marcaigh et al., "Estimating the predictive value of a diagnostic test how to prevent misleading or confusing results." Clinical Pediatrics (1993); 32.8: 485-491.

PCT Application No. PCT/IB2014/002398, International Preliminary Report on Patenability dated Mar. 15, 2016, 5 pages.

PCT Application No. PCT/IB2014/002398, International Search Report and Written Opinion dated Nov. 12, 2014, 8 pages.

PCT Application No. PCT/US2014/054816, International Preliminary Report on Patenability dated Mar. 15, 2016, 6 pages.

PCT Application No. PCT/US2014/054816, International Search Report and Written Opinion dated Nov. 12, 2014, 9 pages.

Pepe et al., "Limitations of the odds ratio in gauging the performance of a diagnostic, prognostic, or screening marker." American Journal of Epidemiology (2004); 159.9: 882-890.

Reiersen, A.M. and Todd, R.D. "Co-occurrence of ADHD and autism spectrum disorders: phenomenology and treatment." Expert Review of Neurotherapeutics (2008); 8(4): 657-669.

Sharma, A., et al. "Dysregulation of mTOR signaling in fragile X syndrome." The Journal of Neuroscience (2010); 30(2): 694-702.

Shultz, "Clinical Interpretation of Laboratory Procedures." Chapter 14 in Teitz, Fundamentals of Clinical Chemistry, Burtis and Ashwood (eds.), 4th Edition (1996), W.B. Saunders Company, pp. 192-199.

Torrioli, MariaGiulia, et al. "Treatment with valproic acid ameliorates ADHD symptoms in fragile X syndrome boys." American Journal of Medical Genetics Part A (2010); 152(6): 1420-1427.

Wang et al., "Activation of the extracellular signal-regulated kinase pathway contributes to the behavioral deficit of fragile x-syndrome." Journal of Neurochemistry (2012); 121(4): 672-679.

Wang, Hoau-Yan, et al. "BDNF-trkB signaling in late life cognitive decline and Alzheimer's disease." Translational Neuroscience (2011); 2(2): 91-100.

Weng, N., et al. "Early-phase ERK activation as a biomarker for metabolic status in fragile X syndrome." American Journal of Medical Genetics Part B: Neuropsychiatric Genetics (2008); 147(B): 1253-1257.

Zweig et al., "ROC curve analysis: an example showing the relationships among serum lipid and apolipoprotein concentrations in identifying patients with coronary artery disease." Clinical Chemistry (1992); 38.8: 1425-1428.

Paul, K, et al., "Dampened dopamine-mediated neuromodulation in prefrontal cortex of fragile X mice." J Physiol (2013); 591.4: 1133-1143.

* cited by examiner

METHODS OF DETERMINING RESPONSE TO THERAPY

RELATED APPLICATIONS

This application is the National Stage of International Patent Application No. PCT/US2014/054816, filed Sep. 9, 2014, which claims priority to and benefit of provisional application U.S. Ser. No. 61/875,384 filed on Sep. 9, 2013, U.S. Ser. No. 14/038,258 filed Sep. 26, 2013 and provisional application U.S. Ser. No. 61/991,351 filed May 9, 2014. The contents of each application listed above are herein incorporated by reference in their entireties.

FIELD OF THE INVENTION

The present invention relates generally to methods of determining the response to metadoxine therapy for the treatment of Fragile X Syndrome and other cognitive disorders. The invention also relates to identifying individuals that will be responsive to metadoxine therapy.

BACKGROUND OF THE INVENTION

Fragile X Syndrome (FXS), as implied by its name, is associated with a fragile site expressed as an isochromatid gap in the metaphase chromosome at map position Xq 27.3. Fragile X syndrome is a genetic disorder caused by a mutation in the 5'-untranslated region of the fragile X mental retardation 1 (FMR1) gene, located on the X chromosome. The mutation that causes FXS is associated with a CGG repeat in the fragile X mental retardation gene FMR1. In most healthy individuals, the total number of CGG repeats ranges from less than 10 to 40, with an average of about 29. In fragile X syndrome, the CGG sequence is repeated from 200 to more than 1,000 times. When a subject has more than about 200 CGG repeats, the fragile X gene becomes hypermethylated, which silences the gene. As a result, fragile X mental retardation protein (FMRP) is not produced, or is produced at reduced level, and the subject displays manifestations of FXS.

Premutation expansions (55-200 CGG repeats) of the FMR1 gene are frequent in the general population, with estimated prevalences of 1 per 259 females and 1 per 812 males. Carriers of the premutation typically have normal IQ, although emotional problems such as anxiety are common. Older male carriers of the premutation (50 years and older) develop progressive intention tremor and ataxia. These movement disorders are frequently accompanied by progressive cognitive and behavioral difficulties, including memory loss, anxiety, and deficits of executive function, reclusive or irritable behavior, and dementia. This disorder has been designated fragile X-associated tremor/ataxia syndrome (FXTAS). Magnetic resonance imaging in subjects with FXTAS reveals increases in T2-weighted signal intensity in the middle cerebellar peduncles and adjacent cerebellar white matter.

FXS segregates as an X-linked dominant disorder with reduced penetrance. Either sex when carrying the fragile X mutation may exhibit intellectual disability, which is variable in severity. Children and adults with FXS have varying degrees of intellectual disability or learning disabilities and behavioral and emotional problems, including autistic-like features and tendencies. Young children with FXS often have delays in developmental milestones, such as learning how to sit, walk and talk. Affected children may have frequent tantrums, difficulties in paying attention, frequent seizures (e.g., temporal lobe seizures), are often highly anxious, easily overwhelmed, can have sensory hyperarousal disorder, gastrointestinal disorders, and may have speech problems and unusual behaviors, such as hand flapping and hand biting.

FXS can be diagnosed by an established genetic test performed on a sample (e.g., blood sample, buccal sample) from the subject. The test determines whether a mutation or pre-mutation is present in the FMR1 gene of the subject based upon the number of CGG repeats.

Subjects with FXS can also have autism. About 5% of all children diagnosed with autism have a mutation in the FMR1 gene and also have fragile X syndrome (FXS). Autism spectrum disorder (ASD) is seen in approximately 30% of males and 20% of females with FXS, and an additional 30% of FXS individuals display autistic symptoms without having the ASD diagnosis. Although intellectual disability is a hallmark feature of FXS, subjects with FXS often display autistic features ranging from shyness, poor eye contact, and social anxiety in mild cases to hand flapping, hand biting and preservative speech in the severely affected. Subjects with FXS display other symptoms associated with autism such as attention deficit and hyperactivity, seizures, hypersensitivity to sensory stimuli obsessive-compulsive behavior and altered gastrointestinal function. The FMR1 mutation prevents or greatly decreases expression of a single protein (FMRP). Brain development in the absence of FMRP is thought to give rise to the major symptoms of FXS.

In addition to core symptoms, children with FXS frequently have serious behavioral disturbances such as irritability, aggression and self-injurious behaviors. In a recent study of males with FXS (ages 8-24), self-injurious behavior was reported in 79%, and aggressive behavior in 75%, of subjects during a two month observation period.

Currently available treatment regimens for humans with FXS include, for example, behavioral modifications and treatment with a range of medications (not approved by FDA for the treatment of FXS) including antidepressant and antipsychotic drugs. Cognitive behavioral therapy has been used to improve language and socialization in individuals with FXS and autism. In recent years, pharmacological treatment with the atypical antipsychotic risperidone has been commonly employed to augment non-pharmacological approaches in the treatment of individuals with autism. A randomized placebo-controlled trial of risperidone in autistic children demonstrated significant improvement on the irritability subscale of the Aberrant Behavior Checklist and the Clinical Global Impressions-Improvement (McCracken, J. T., et al., N. Engl. J. Med. 347:314-321 (2002)). However, adverse events included weight gain, increased appetite, fatigue, drowsiness, dizziness, and drooling. Social isolation and communication were not improved by administration of risperidone and adverse side effects such as extrapyramidal symptoms and dyskinesias have been associated with risperidone use in autistic children.

SUMMARY OF THE INVENTION

The invention provides methods of assessing the effectiveness of a metadoxine treatment regimen in a subject having Fragile X Syndrome or other cognitive disorder who has received the metadoxine treatment, by measuring the amount of phosphorylated ERK and Akt protein in a sample derived from the subject; measuring the total amount of ERK and Akt protein in the sample; calculating a ratio of the amount of phosphorylated ERK and Akt protein to the total amount of ERK and Akt protein and comparing the calculated ratio to a calculated ratio measured from a non-diseased subject. When the calculated ratio of the subject is similar to the calculated ratio for a known non-diseased subject, the treatment is effective.

Also provided by the invention are methods of determining whether a subject with Fragile X Syndrome or other cognitive disorder would derive a benefit from a metadoxine treatment regimen by measuring the amount of phosphorylated ERK and Akt protein in a sample derived from the subject; measuring the total amount of ERK and Akt protein in the sample; calculating a ratio of the amount of phosphorylated ERK and Akt protein to the total amount of ERK and Akt protein and comparing the subject calculated ratio to a calculated ratio measured from a non-diseased subject. When the subject calculated ratio is higher than the calculated ratio of a known non-diseased subject, the subject would derive a benefit from the metadoxine treatment regimen.

Also provided by the invention are methods of monitoring a metadoxine treatment regimen in a subject having Fragile X Syndrome or other cognitive disorder, by measuring the amount of phosphorylated ERK and Akt proteins in a first sample from the subject at a first period of time; measuring the total amount of ERK and Akt protein in the first sample at the first period of time; calculating a first ratio of the amount of phosphorylated ERK and Akt protein to the total amount of ERK and Akt protein; measuring the amount of phosphorylated ERK and Akt protein in a second sample from the subject at a second period of time; measuring the total amount of ERK and Akt protein in the second sample at the second period of time; calculating a second ratio of the amount of phosphorylated ERK and Akt proteins to the total amount of ERK and Akt proteins and comparing the first ratio to the second ratio. When the second ratio is lower than the first ratio, the treatment is effective.

In some aspects the measuring steps comprise an immunoassay. In some embodiments the sample is whole blood or a fraction thereof. In some embodiments the sample is a peripheral blood mononucleated cell (PBMC). In some embodiments the PBMC is a lymphocyte or a monocyte.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

Figure 11:
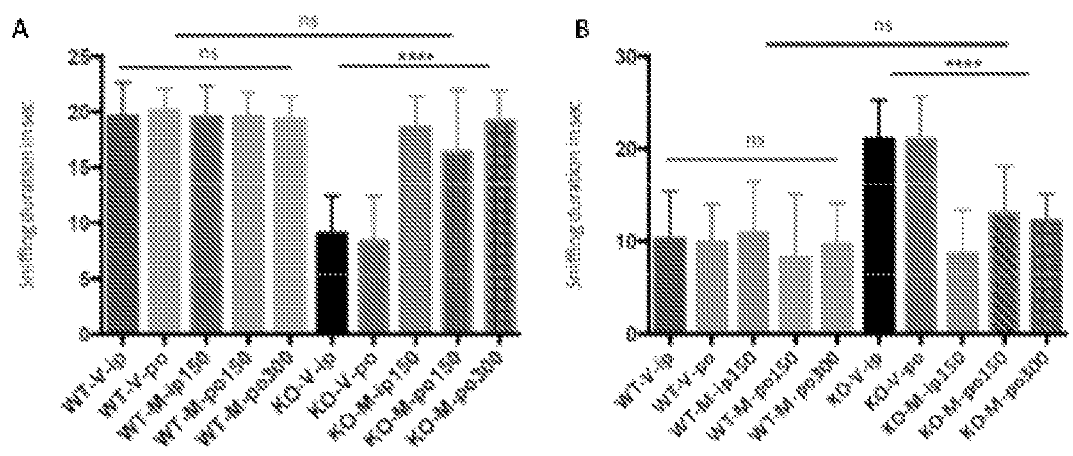

FIG. 11 shows the effect of once daily ip or oral administration (po) of vehicle (V) or metadoxine (M) at 150 or 300 mg/kg for 7 days on social approach (Panel A) and social memory (Panel B) in 2 month old Fmr1 knockout (KO) or Wild Type (WT) mice. Data shown are mean±sem, N=10 mice per group. p<0.01, **p<0.0001, and ns=Not Significant.

Figure 12:
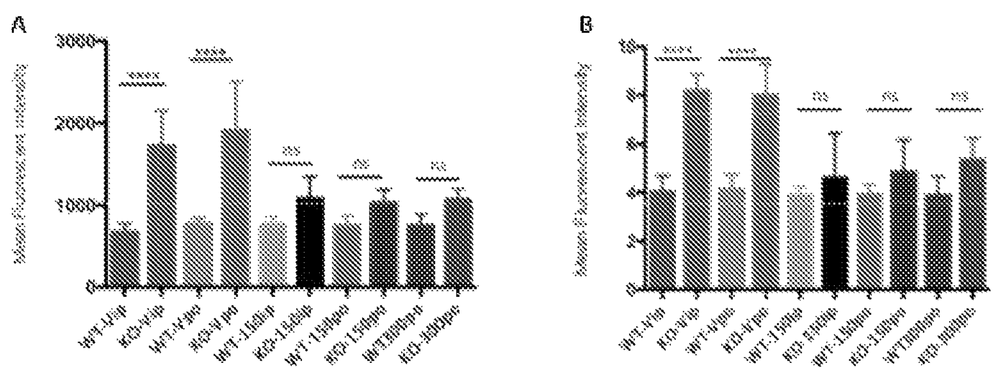

FIG. 12 shows the effect of once daily ip or oral administration (po) of vehicle (V) or metadoxine (M) at 150 or 300 mg/kg for 7 days on lymphocyte biomarkers as assessed using flow cytometry in 2 month old Fmr1 knockout (KO) and Wild Type (WT) mice. Biomarkers shown are pAkt (Panel A) and pERK (Panel B) in Fmr1 knockout or Wild Type mice. Data shown are mean±sem. N=10 mice per group. ****p<0.0001 and ns=Not Significant.

Figure 13:
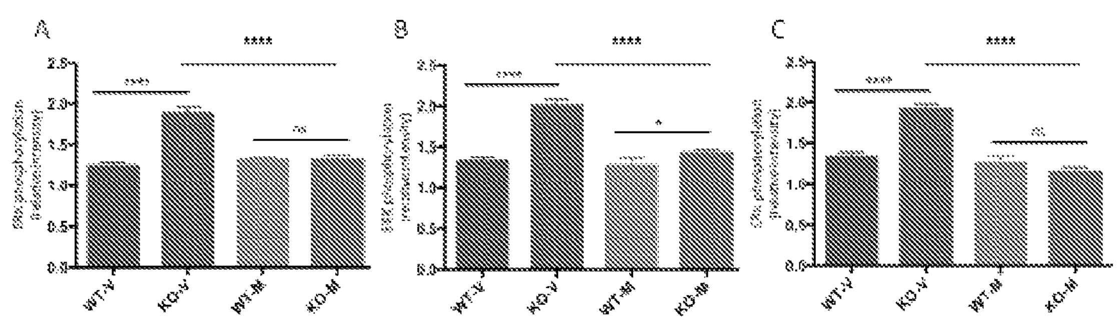

FIG. 13 shows the effect of once daily ip of vehicle (V) or 150 mg/kg metadoxine (M) for 7 days on pERK levels in brain regions of two month old Wild Type (WT) and Fmr1 knockout (KO) mice. The regions analyzed were the hippocampus (Panel A), pre-frontal cortex (Panel B), and striatum (Panel C) in Fmr1 knockout or Wild Type mice. Data shown are mean±sem, N=10 mice per group. ****p<0.0001 and ns=Not Significant.

Figure 14:
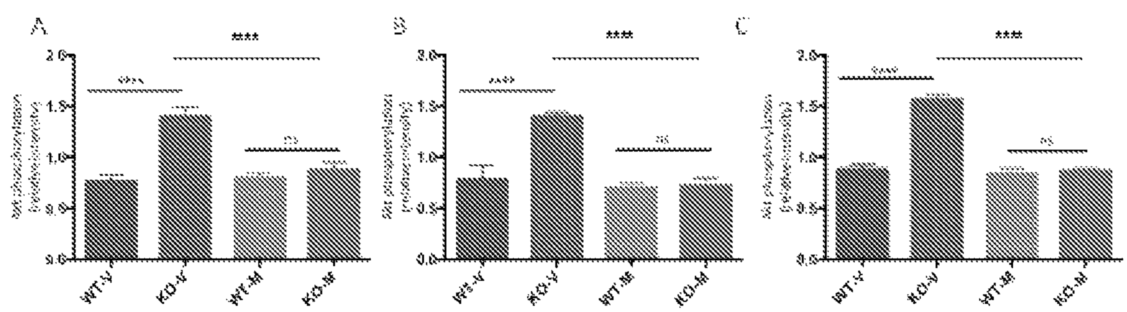

FIG. 14 shows the effect of once daily ip of vehicle (V) or 150 mg/kg metadoxine (M) for 7 days on pAkt levels in brain regions of two month old Wild Type (WT) and Fmr1 knockout (KO) mice. The regions analyzed were the hippocampus (Panel A), pre-frontal cortex (Panel B), and striatum (Panel C) in Fmr1 knockout or Wild Type mice. Data shown are mean±sem, N=10 mice per group. ****p<0.0001 and ns=Not Significant.

Figure 15:
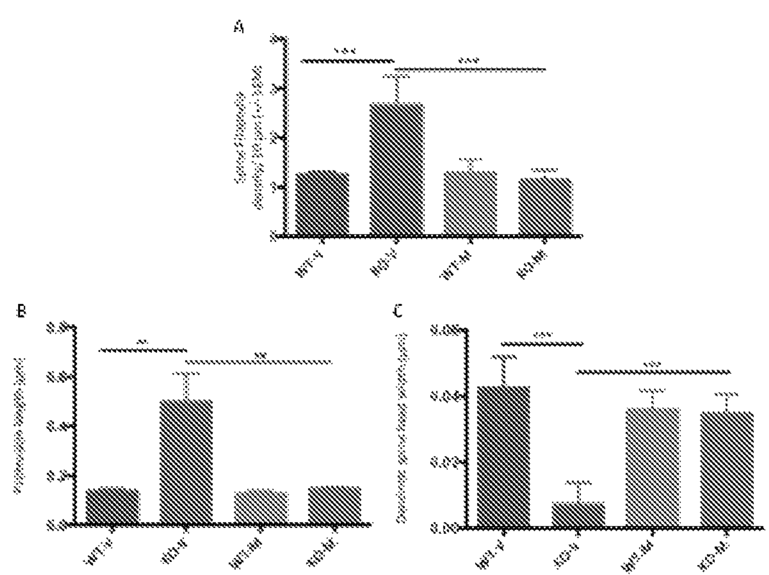

FIG. 15 shows the effect of 5 hour treatment with vehicle (V) or 300 μM metadoxine (M) in vitro on filopodia density (Panel A), length (Panel B), and width (Panel C) in neuronal hippocampal cultures from Fmr1 knockout (KO) or Wild Type (WT) mice. Data shown are mean±sem, (Wild Type, N=20 neurons and Fmr1 knockout mice, N=20 neurons).  p<0.01, *p<0.001, and ns=Not Significant.

Figure 16:
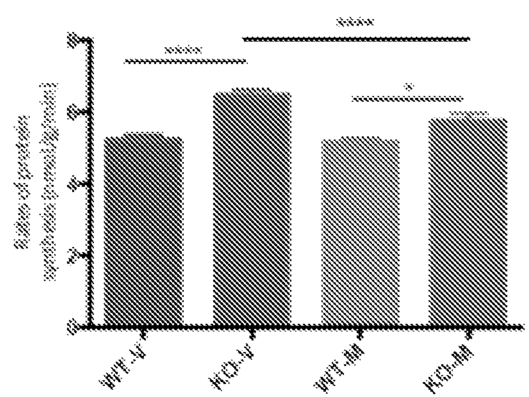

FIG. 16 shows the effect of treatment in vitro with vehicle (V) or 300 μM metadoxine (M) on basal de novo protein synthesis in 400 μM hippocampal slices from Fmr1 knockout (KO) or Wild Type (WT) mice. Data shown are mean±sem, N=6 slices per group. *p<0.001 and ****p<0.0001.

DETAILED DESCRIPTION OF THE INVENTION

The present invention relates to the identification of biomarkers associated with the response to metadoxine therapy for individuals with Fragile X Syndrome (FXS) and other cognitive disorders. Specifically, it was discovered that metadoxine treatment returns the ratio of phosphorylated ERK and Akt protein to total ERK and Akt protein in a subject sample closer to normal ratios. By normal ratios it is meant the ratio of phosphorylated ERK and Akt protein to total ERK and Akt protein found in normal (i.e, non-diseased) subjects. Furthermore, it was unexpectedly discovered that these alterations in phosphorylated ERK and Akt protein to total ERK and Akt protein ratio could be detected in the blood.

Accordingly, the invention provides methods for monitoring subjects undergoing metadoxine treatment for FXS or other cognitive disorders by determining the ratio of phosphorylated ERK and Akt proteins to total ERK and Akt protein in a subject sample. The ratio is compared to a control ratio, such as the ratio obtained from a subject not afflicted with the cognitive disorder. A subject ratio similar to a normal control ratio indicates that the treatment is efficacious.

Additionally the invention provides methods of selecting subjects who have cognitive disorders that would derive a benefit from metadoxine treatment, by determining the ratio of phosphorylated ERK or Akt protein to total ERK and Akt protein in a subject sample. The ratio is compared to a control ratio, such as the ratio obtained from a subject not afflicted with the cognitive disorder. A subject ratio greater than a normal control ratio indicates that the subject may derive a benefit from metadoxine treatment. Whereas subjects that do not have a ratio greater than a normal control ratio may not derive a benefit from metadoxine treatment Although calculation of the ratio is described one way herein, it is to be understood to encompass calculating the inverse as is apparent to a person of ordinary skill. Also, whereas calculation of ratios as described herein is beneficial in providing useful comparative numbers, calculation of absolute differences between phosphorylated ERK and Akt protein and total ERK and Akt proteins levels, and between test subjects and control subjects, could also be employed and would be effectively used in practicing the invention.

Definitions

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"Biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as "clinical parameters" defined herein, as well as "traditional laboratory risk factors", also defined herein. Biomarkers also include any calculated indices created mathematically or combinations of any one or more of the foregoing measurements, including temporal trends and differences. Where available, and unless otherwise described herein, biomarkers which are gene products are identified based on the official letter abbreviation or gene symbol assigned by the international Human Genome Organization Naming Committee (HGNC) and listed at the date of this filing at the US National Center for Biotechnology Information (NCBI) web site.

A "Clinical indicator" is any physiological datum used alone or in conjunction with other data in evaluating the physiological condition of a collection of cells or of an organism. This term includes pre-clinical indicators.

"Clinical parameters" encompasses all non-sample or non-analyte biomarkers of subject health status or other characteristics, such as, without limitation, age (Age), ethnicity (RACE), gender (Sex), or family history (FamHX).

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful either combined with a selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4.sup.th edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronary Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935. Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present invention, relates to the probability that an event will occur over a specific time period, as in the responsiveness to treatment, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion.

"Risk evaluation" or "evaluation of risk" in the context of the present invention encompasses making a prediction of the probability, odds, or likelihood that an event or disease state may occur, the rate of occurrence of the event or conversion from one disease state. Risk evaluation can also comprise prediction of future clinical parameters, traditional laboratory risk factor values, or other indices of FXS, either in absolute or relative terms in reference to a previously measured population. The methods of the present invention may be used to make continuous or categorical measurements of the responsiveness to treatment thus diagnosing and defining the risk spectrum of a category of subjects defined as being responders or non-responders. In the categorical scenario, the invention can be used to discriminate between normal and other subject cohorts at higher risk for responding.

A "sample" in the context of the present invention is a biological sample isolated from a subject and can include, by way of example and not limitation, whole blood, serum, plasma, cerebrospinal fluid (CSF), brain cells, or any other secretion, excretion, or other bodily fluids. A "sample" may include a single cell or multiple cells or fragments of cells. The sample is also a tissue sample. The sample is or contains a brain cell or a lymphocyte. Preferably the sample is peripheral blood mononuclear cell such as a lymphocyte or monocyte.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is considered highly significant at a p-value of 0.05 or less. Preferably, the p-value is 0.04, 0.03, 0.02, 0.01, 0.005, 0.001 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of FXS. A subject can be male or female. The subject has or is suspected of having FXS or other cognitive disorders.

"TN" is true negative, which for a disease state test means classifying a non-disease or normal subject correctly.

"TP" is true positive, which for a disease state test means correctly classifying a disease subject.

"Traditional laboratory risk factors" correspond to biomarkers isolated or derived from subject samples and which are currently evaluated in the clinical laboratory and used in traditional global risk assessment algorithms. Other traditional laboratory risk factors for Fragile X known to those skilled in the art.

Methods of the Invention

The methods disclosed herein are used with subjects undergoing metadoxine treatment and/or therapies for FXS and other cognitive disorders and for subjects who have been diagnosed with FXS and other cognitive disorders.

The methods of the present invention are useful to monitor the treatment of FXS and other cognitive disorders in a subject and to select subjects who would derive a benefit from metadoxine treatment.

In general, the signs and symptoms of FXS fall into five categories: intelligence and learning; physical, social and emotional, speech and language and sensory disorders commonly associated or sharing features with Fragile X. For example, individuals with FXS have impaired intellectual functioning, social anxiety, language difficulties and sensitivity to certain sensations.

Cognitive disorders include the group of disorders in which a dysfunction/impairment of mental processing constitutes the core symptomatology. Cognitive disorders include neurogenetic cognitive disorders or behavioral cognitive disorders Cognitive disorders include developmental disorders, attention deficit hyperactivity disorder (ADHD), autism spectrum disorders, Alzheimers disease, schizophrenia and cerebrovascular disease.

Autism spectrum disorders and autistic symptoms are commonly associated with individuals with Fragile X syndrome. Signs and symptoms of autism include significant language delays, social and communication challenges, and unusual behaviors and interests. Many people with autistic disorder also have intellectual disability.

Determination of the ratio of phosphorylated ERK and Akt protein to total ERK and Akt protein in a subject sample allows for the course of treatment of FXS or other cognitive disorder to be monitored. In this method, a biological sample is provided from a subject undergoing treatment. If desired, biological samples are obtained from the subject at various time points before, during, or after treatment. The ratio of phosphorylated ERK and Akt protein to total ERK and Akt protein are then calculated and compared to a control value. A control value is a control individual or population whose ratio of phosphorylated ERK and Akt protein to total ERK and Akt protein state is known or an index value. The reference sample or index value may be taken or derived from one or more individuals who are not diseased (e.g., not affected with the FXS or other cognitive disorder). Alternatively, the reference sample or index value may be taken or derived from the subject before treatment. For example, samples may be collected from a subject who has not received an initial treatment and after subsequent treatment to monitor the progress of the treatment. The reference sample or index value may be taken or derived from the subject after the initial treatment. For example, samples may be collected a subject who have received initial treatment and subsequent treatment for FXS to monitor the progress of the treatment.

In another embodiment, the reference value is an index value or a baseline value. An index value or baseline value is a composite sample of the ratio of phosphorylated ERK and Akt protein to total ERK and Akt protein from individuals that do not suffer from FXS or other cognitive disorder.

The effectiveness of treatment can be monitored by determining the ratio of phosphorylated ERK and Akt protein to total ERK and Akt protein in a sample obtained from a subject over time and comparing the ratios. For example, a first sample can be obtained prior to the subject receiving treatment and one or more subsequent samples are taken after or during treatment of the subject.

By "efficacious", it is meant that the treatment leads to a ratio of phosphorylated ERK and Akt protein to total ERK and Akt protein similar to that from a subject that does not have FXS or other cognitive disorder. Efficacy can be determined in association with any known method for diagnosing, identifying, or treating FXS.

Phosphorylated ERK and Akt and total ERK and Akt protein can be determined by any method known in the art, such as immunoassay.

Performance and Accuracy Measures of the Invention

The performance and thus absolute and relative clinical usefulness of the invention may be assessed in multiple ways as noted above. The accuracy of a diagnostic, predictive, or prognostic test, assay, or method concerns the ability of the test, assay, or method to distinguish between subjects responsive to metadoxine treatment and those that are not, is based upon the ratio of phosphorylated ERK and Akt protein to total ERK and Akt protein. The difference in the ratio between normal and abnormal is preferably statistically significant.

Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

Using such statistics, an "acceptable degree of diagnostic accuracy", is herein defined as a test or assay in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.80, desirably at least 0.85, more desirably at least 0.875, preferably at least 0.90, more preferably at least 0.925, and most preferably at least 0.95.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for therapeutic unresponsiveness, and the bottom quartile comprising the group of subjects having the lowest relative risk for therapeutic unresponsiveness Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future events. Often such lower diagnostic accuracy tests must be combined with additional parameters in order to derive meaningful clinical thresholds for therapeutic intervention, as is done with the aforementioned global risk assessment indices.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

Construction of Clinical Algorithms

Any formula may be used to combine results into indices useful in the practice of the invention. As indicated above, and without limitation, such indices may indicate, among the various other indications, the probability, likelihood, absolute or relative chance of responding to metadoxine. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and accuracy characteristics of its results in a training population. Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. “Important” is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual phosphorylation of ERK and/or Akt measurement into more valuable forms of information, prior to their presentation to the predictive formula. Most notably, normalization of biomarker results, using either common mathematical transformations such as logarithmic or logistic functions, as normal or other distribution positions, in reference to a population’s mean values, etc. are all well known to those skilled in the art. Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population’s expected prevalence and mean biomarker parameter values, according to the technique outlined in D’Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula. An example of this is the presentation of absolute risk, and confidence intervals for that risk, derived using an actual clinical study, chosen with reference to the output of the recurrence score formula in the Oncotype Dx product of Genomic Health, Inc. (Redwood City, Calif.). A further modification is to adjust for smaller sub-populations of the study based on the output of the classifier or risk formula and defined and selected by their Clinical Parameters, such as age or sex.

EXAMPLES

Example 1: General Methods

The examples as described herein were performed using the reagents and methods generally described below.

Experimental Animals

Fmr1 knockout mice (KO2) mice (The Dutch-Belgium Fragile X Consortium, 1994), initially obtained from the Jackson Laboratory, and wild type (WT) littermates were generated on a C57BL/6J background and repeatedly backcrossed onto a C57BL/6J background for more than eight generations. The Fmr1 knockout mice were housed in groups of the same genotype in a temperature and humidity controlled room with a 12-h light-dark cycle (lights on from 7 am to 7 pm; testing was conducted during light phase). Room temperature and humidity were recorded continuously in the holding room while food and water were available ad libitum. Testing was conducted on healthy Fmr1 knockout mice and their wild type littermates (N=10 mice per treatment group) at 2 or 6 months of age during the behavioral experiments. Mice were housed in commercial plastic cages and experiments were conducted in line with the requirements of the UK Animals (Scientific Procedures) Act, 1986. All experiments were conducted with experimenters blind to genotype and drug treatment. Animals were allowed a minimum acclimatization period of one week prior to performing any experiment. No prophylactic or therapeutic treatment was administered during the acclimatization period.

Drugs

For Study 1 (Example 2), metadoxine was dissolved in saline and administered intraperitoneally at doses of 100, 150, or 200 mg/kg/once daily for 7 days. For Study 2 (Example 3), in vivo testing, metadoxine was dissolved in saline and administered at an intraperitoneal dose of 150 mg/kg per day or at an oral dose of 150 or 300 mg/kg/day (in a volume of 0.1 ml) once daily for seven days. For Study 2, in vitro testing, metadoxine was administered at concentration of 300 μM for five hours. In all cases, saline was used as a vehicle (control).

Behavioral Testing

Social Interaction and Social Recognition Memory:

Mice are a social species that engage in easily scored social behaviors including approaching, following, sniffing, grooming, aggressive encounters, sexual interactions, parental behaviors, nesting, and sleeping in a group huddle. Social approach in mice was evaluated by sniffing duration directed to a novel mouse.

Mice were placed in a test arena/cage of the same order of magnitude in size as the adult's home cage (40×23×12 cm cage, with a Perspex lid to facilitate viewing the mice) with fresh wood chippings on the floor. A background mouse odor was created by putting in some non-experimental mice into the apparatus prior to testing. Mice were transferred to the experimental room 10-15 min prior to testing. A test subject and a juvenile were placed simultaneously into the test cage. The total duration and number of bouts of social investigation, defined as sniffing and close following (<2 cm from the tail) of the stimulus juvenile by the tested mouse, was assessed for 3 min. 30 min later, the test was repeated using the same stimulus juvenile. Data parameters collected were the total duration and total number of bouts of sniffing for the acquisition and recognition. A social memory ratio was derived, defined as trial 2/trial 1+2. Therefore, no memory (e.g. 20/(20+20)=0.5 and memory (e.g. 10/(20+10)=<0.5.

Y-Maze Alternation:

Two tasks were implemented. The first was an unlearned assessment of spontaneous alternation between arm entries. The second was a spatial reference memory task in which the animal had to learn which of the two arms was baited with a food reward. The day prior to the start of the training, mice were allowed to freely explore the maze for 5 min. Next, they received two trials, one in which the food was located on the left arm and one in which the food was positioned on the right arm. This procedure prevented the development of a preference for one of the arms.

Y-Maze Water Maze:

A clear Perspex Y-maze was filled with 2 cm of water at 20° C. This motivated the mouse to leave the maze after paddling to an exit tube at the distal end of one arm. The maze was placed in the middle of a room surrounded by prominent visual cues.

Rewarded T Maze Alternation:

An elevated or enclosed apparatus in the form of a T (placed horizontally) was used. Mice were placed at the base of the T and were allowed to choose one of the goal arms abutting the other end of the stem. Two trials were conducted in quick succession, the second trial required mice to choose the arm not visited before, reflecting memory of the first choice (spontaneous alternation). This tendency was reinforced by making the animal hungry and rewarding it with a preferred food if it alternated. Specifically, after a four day habituation period on the T-maze, mice were trained to alternate arm choices to receive sweet condensed milk as reward.

Successive Alleys:

The apparatus consisted of four successive, linearly arranged, increasingly anxiogenic alleys (each succeeding alley was painted a lighter color, had lower walls and/or was narrower than the previous alley) made of painted wood. Each section or alley was 25 cm long. Alley 1 had 25 cm high walls, was 8.5 cm wide, and was painted black. A 0.5 cm step down led to alley 2, which was again 8.5 cm wide, but had 1.3 cm high walls and was grey. A 1.0 cm step down led to alley 3, which was 3.5 cm wide, had 0.8 cm high walls, and was white. A 0.4 cm step led down to alley 4, which was also white, but had 1.2 cm wide and 0.2 cm high walls. The apparatus was elevated by anchoring the back of alley 1 to a stand, 50 cm high. Padding was provided under arms 3 and 4 in case a mouse fell off. Each mouse was placed at the closed end of alley 1 facing the wall. Timers were started 1) for the overall length of the test (5 min)+the latency to enter each arm, and 2) for the time spent in alley 1. When the mouse placed all 4 feet on to the next alley, it was considered to have entered the alley. Total time spent in each alley (all four feet) was recorded.

Contextual Fear Conditioning:

In the fear conditioning experiment, mice were placed into a novel environment (dark chamber) and received pairings of a cue and electric footshock (0.2 mA for 1 sec (Study 1) or 0.7 mA for 0.5 sec (Study 2)). Subsequently, when tested in the original training context, mice displayed a natural defensive response termed freezing (Blanchard, 1969) or contextual fear conditioning. Freezing time was defined as the time that the mice spent in immobile behavior, except for respiration. The data was expressed as the percentage of the test period. 24 hours after a training session, mice were tested for 5 min in the training chamber with no shock presentation and observed for freezing behavior.

Statistics:

Multivariate analysis of variance was employed to assess group differences across data. Repeated measures ANOVA were performed for behavioral data. Statistically significant effects in each ANOVA were followed with post hoc comparisons, using the Newman-Keuls test (Study 1) or the Tukey test (Study 2). A p value of less than 0.05 was considered significant.

Biochemical Testing

Phosphorylated ERK and Akt:

The Ras-Mek-ERK and PI3K-Akt-mToR signaling pathways are involved in mediating activity dependent alterations in gene transcription underlying changes in synaptic plasticity (Klann and Dever, 2004). Phosphorylated ERK and Akt protein expression was measured by western blot analysis as previously described by Lopez Verrilli (Lopez Verrilli et al., 2009). The antibodies employed were anti-phosphospecific antibodies against Akt (1/1000) and kinase (ERK) 1/2 (1/2000) (Cell Signaling Technology, Danvers, Mass., USA). The antibody against phospho-ERK detects phosphorylation at phospho-ERK1/2 (Thr202/Tyr204) whereas the antibody against phospho-Akt detects phosphorylation at phospho-Akt (Thr308). Total Akt and ERK 1/2 protein content and phosphorylated ERK and Akt were evaluated by blotting membranes with antiphospho-Akt (1/1000) and antiphospho-ERK antibodies (1/2000) (Cell Signaling Technology, Danvers, Mass., USA). Akt or ERK phosphorylation was normalized to protein content in the same sample and expressed as % of change with respect to basal conditions, considering basal levels as 100%. Protein loading was evaluated by stripping and re-blotting membranes with β-actin antibody (1/1000) (Sigma-Aldrich, St. Louis, Mo., USA). Phosphorylated ERK and Akt protein expression in blood lymphocytes was measured by flow cytometry. For lymphocyte biomarker determinations, a FACStar plus (Becton Dickinson) was used with the excitation laser tuned at 488 nm and green fluorescence from FITC (GST) was collected through a 515-545 nm bandpass filter. The mean FITC fluorescence Intensity was calculated in relation to the fluorescence of reference cells. The mean cellular fluorescence intensity (MFI) is directly proportional to the mean number of Ab molecules bound per cell.

Neuronal Morphology:

Hippocampal cell cultures were prepared from wild type and Fmr1 KO fetal mice at embryonic day of gestation 17.5 (E 17.5). Mice were killed by cervical dislocation and dissociated hippocampal cells were plated in 15 mm multi well vessels (Falcon Primaria). After 5 d in vitro, green fluorescent protein (GFP) was transfected to facilitate monitoring dendritic spine morphogenesis after drug treatment (Ethell and Yamaguchi, 1999; Ethell et al., 2001, Henkemeyer et al., 2003). Dendritic spines were formed at around 16 days in vitro (DIV). Cultures were treated with metadoxine at 300 μM concentration at day 17 in vitro for 5 hrs.

Filopodia density of GFP transfected neurons was quantified by performing Sholl analyses of stacked Zeiss confocal generated images (40×objective, stack of 20×0.2 μm). With Metamorph software, concentric equally spaced circles (every 20 μm) were drawn around the cell soma of each neuron and subsequently, the amount of filopodia was counted per circle. Averages of counts were compared with unpaired two-tailed Student's T-tests.

Spine maturity of GFP transfected neurons was analyzed with Metamorph software (Molecular Devices, Sunnyvale, Calif.). Two distal dendritic segments of 70 100 μm were chosen per neuron for spine morphometric analysis. For each spine, the length and the width were measured. The length was defined as the distance from the base to the tip of the protrusion; whereas width was defined as the maximum distance perpendicular to the long axis of the spine. Measurements were compared with unpaired two tailed Student's T-tests and ANOVA corrected for multiple comparisons.

De Novo Hippocampal Protein Synthesis:

Transverse hippocampal slices (400 μm) were obtained from 6-week-old Fmr1 knockout and WT mice. A protein synthesis assay was performed as previously described using the nonradioactive fluorescence-activated cell sorting-based assay, surface sensing of translation (SUnSET) method, which allows the monitoring and quantification of global protein synthesis in individual mammalian cells and in heterogeneous cell populations. (Hoeffer, 2011). The concentration of metadoxine used in this study was 300 μM.

Example 2: The Effect of Metadoxine (100 to 200 mg/kg) Treatment on Learning and Memory Deficits and Biochemical Abnormalities in the Fmr1 Knockout Mouse Model of Fragile X Syndrome (Study 1)

Behavioral Analyses

Figure 1:
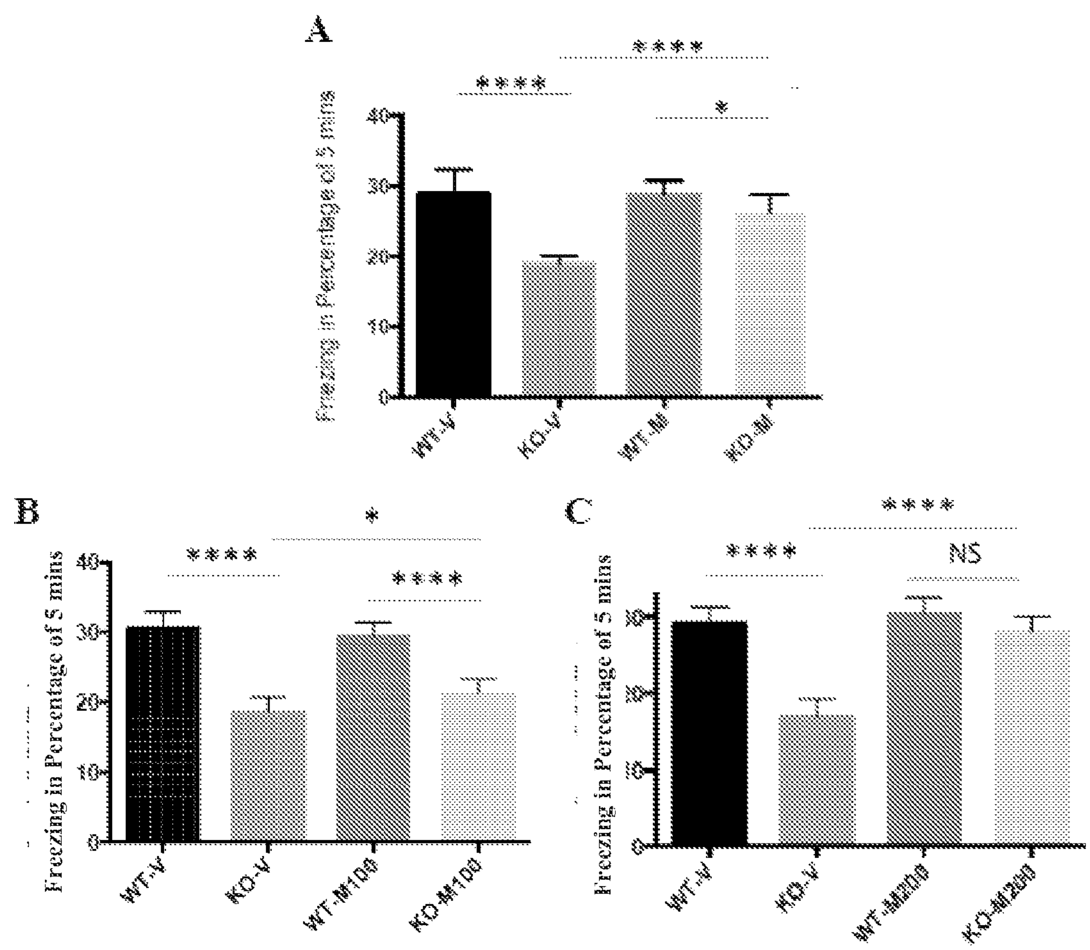
FIG. 1 shows the effect of seven days of once daily intraperitoneal (ip) administration of vehicle (V) or metadoxine (M) (100, 150, or 200 mg/kg) in 2-months old Fmr1 knockout (KO) or Wild Type (WT) mice on contextual fear conditioning. Specifically, Panel A shows the effect of vehicle or 150 mg/kg of metadoxine. Panel B shows the effect of vehicle or 100 mg/kg of metadoxine. Panel C shows the effect of vehicle or 200 mg/kg of metadoxine. Data shown are mean±standard error of the mean (sem), N=10 mice per group. *p<0.05, ****p<0.0001, and NS=Not Significant.

Contextual Fear Conditioning:

An initial experiment tested the effect of intraperitoneal administration of vehicle or 150 mg/kg metadoxine once daily for seven days on contextual fear conditioning in groups of N=10 WT and Fmr1 knockout mice. Vehicle-treated Fmr1 knockout mice showed a deficit in learning in the contextual fear conditioning paradigm as reflected in a reduction in freezing during the test session (FIG. 1, Panel A ($p<0.0001$)). Metadoxine administration reversed the learning deficit effect in Fmr1 knockout mice, this reversal being partial such that metadoxine-treated animals differed from the metadoxine-treated WT animals ($p<0.05$). A replication of this experiment investigated the dose-dependent effects of intraperitoneal administration of vehicle, 100, or 200 mg/kg metadoxine once daily for seven days on contextual fear conditioning in groups of N=10 WT and Fmr1 knockout mice (FIG. 1, Panels B and C). In this experiment, vehicle-treated Fmr1 knockout mice showed a learning deficit compared to vehicle-treated WT mice ($p<0.0001$), replicating the first experiment. 100 mg/kg metadoxine produced a reversal of the deficit in Fmr1 knockout mice ($P<0.05$) but this was a partial reversal since metadoxine-treated Fmr1 knockout mice differed from the metadoxine-treated Wild Type mice ($p<0.0001$). The learning deficit seen in Fmr1 knockout mice was completely reversed following treatment with 200 mg/kg i.p. metadoxine (treated Fmr1 mice differed from vehicle-treated Fmr1 knockout mice ($P<0.0001$) but did not differ from metadoxine-treated WT mice). Metadoxine treatment had no effect on WT mice in either experiment (FIG. 1. Panels A-C).

Figure 2:
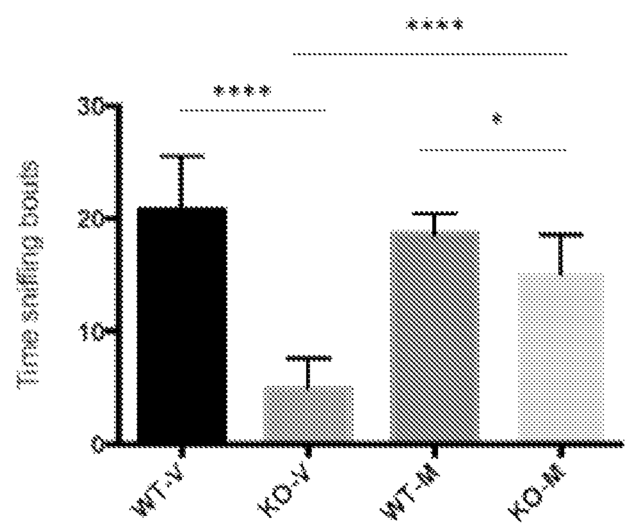
FIG. 2 shows the effect of seven days of once daily intraperitoneal administration of vehicle (V) or 150 mg/kg metadoxine (M) in 2-months old Fmr1 knockout (KO) or Wild Type (WT) mice on social approach behavior. Data shown are mean±sem. N=10 mice per group. * p<0.05 and ****p<0.0001.

Social Approach:

Vehicle-treated Fmr1 knockout mice showed less social approach as indexed by sniffing bouts (FIG. 2 ($p<0.0001$)). Once daily intraperitoneal treatment with 150 mg/kg metadoxine for seven days increased social approach in Fmr1 knockout mice ($p<0.0001$ compared to vehicle treated Fmr1 knockout mice). Fmr1 knockout mice treated with metadoxine differed from metadoxine-treated WT mice ($p<0.05$), although there was a trend approaching the effect of the WT mice. Metadoxine treatment had no effect on WT mice.

Figure 3:
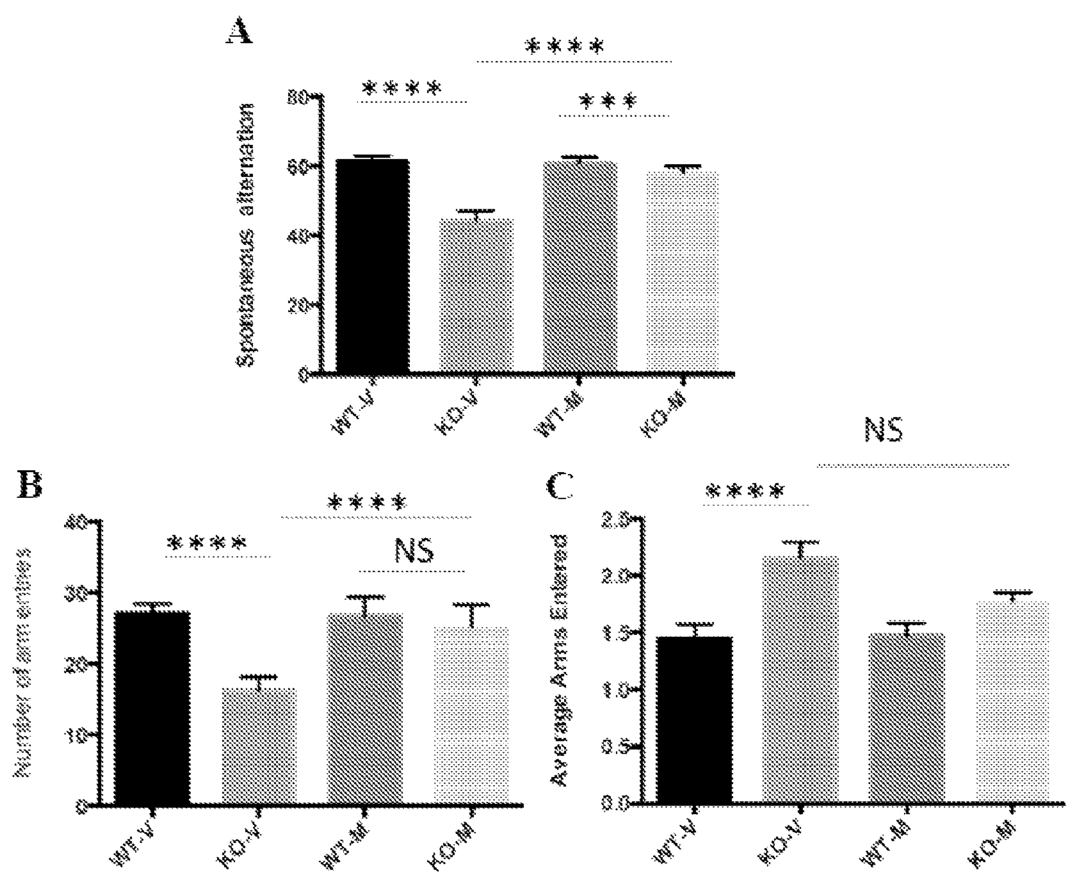
FIG. 3 shows the effect of seven days of once daily intraperitoneal administration of vehicle (V) or 150 mg/kg metadoxine (M) on Y-maze spontaneous alternation (Panel A), Y-maze rewarded alternation (Panel B) or Y-maze water maze spatial discrimination (Panel C) in 2-months old Fmr1 knockout (KO) or Wild Type (WT) mice. Data shown are mean±sem, N=10 mice per group. *p<0.001, **p<0.0001, and NS=Not Significant.

Y-Maze Spontaneous Alternation:

The effect of seven days of once daily treatment with vehicle or 150 mg/kg metadoxine on spontaneous alternation in groups of N=10 WT or Fmr1 knockout mice is shown in FIG. 3, Panel A. Vehicle-treated Fmr1 knockout mice showed less spontaneous alternation than vehicle treated WT mice ($p<0.0001$). Metadoxine treatment increased spontaneous alternation compared to vehicle treatment in Fmr1 knockout mice ($p<0.0001$), although metadoxine-treated Fmr1 knockout mice showed a deficit compared to metadoxine-treated WT mice ($p<0.01$). Metadoxine therefore produced a partial reversal of the deficit seen in Fmr1 knockout mice.

Y-Maze Reference Memory Task:

The effect of seven days of once daily treatment with vehicle or 150 mg/kg metadoxine on rewarded reference memory learning in groups of N=10 WT or Fmr1 knockout mice is shown in FIG. 3, Panel B. Vehicle-treated Fmr1 knockout mice made less appropriate arm entries than vehicle-treated WT mice ($p<0.0001$). Metadoxine treatment reduced this deficit ($p<0.0001$) compared to vehicle-treated Fmr1 knockout mice, such that metadoxine-treated Fmr1 knockout mice did not differ from metadoxine-treated WT mice. Metadoxine treatment had no effect on WT mice.

Y-Maze Water Maze Left Right Discrimination:

The effect of seven days of once daily treatment with vehicle or 150 mg/kg metadoxine on aversively motivated spatial discrimination learning in groups of N=10 WT or Fmr1 knockout mice is shown in FIG. 3, Panel C. Vehicle-treated Fmr1 knockout mice showed a greater number of incorrect arm entries than vehicle-treated WT mice. This deficit was reduced by treatment with metadoxine.

Figure 4:
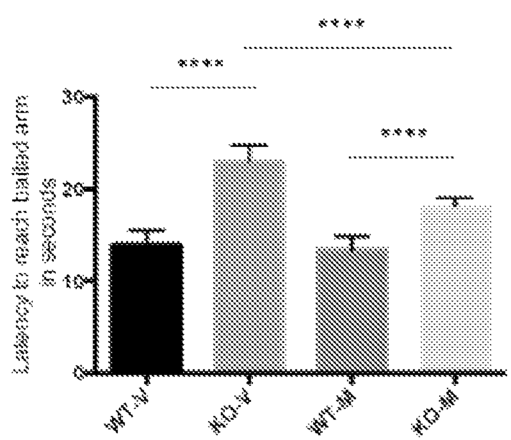
FIG. 4 shows the effect of seven days of once daily intraperitoneal administration of vehicle (V) or 150 mg/kg metadoxine (M) on T-maze rewarded alternation in 2-months old Fmr1 knockout (KO) or Wild Type (WT) mice. Data shown are mean±sem, N=10 mice per group. ****p<0.0001.

T-Maze Rewarded Alternation Task:

The effect of seven days of once daily treatment with vehicle or 150 mg/kg metadoxine on rewarded alternation working memory in groups of N=10 WT or Fmr1 knockout mice is shown in FIG. 4. Vehicle-treated Fmr1 knockout mice showed a greater latency to reach the correct arm compared to vehicle-treated WT mice ($p<0.0001$). Metadoxine treatment reduced this deficit compared to vehicle treatment in Fmr1 knockout mice ($p<0.0001$), this reversal being partial since metadoxine-treated Fmr1 knockout mice responded more slowly than WT mice ($p<0.0001$).

Figure 5:
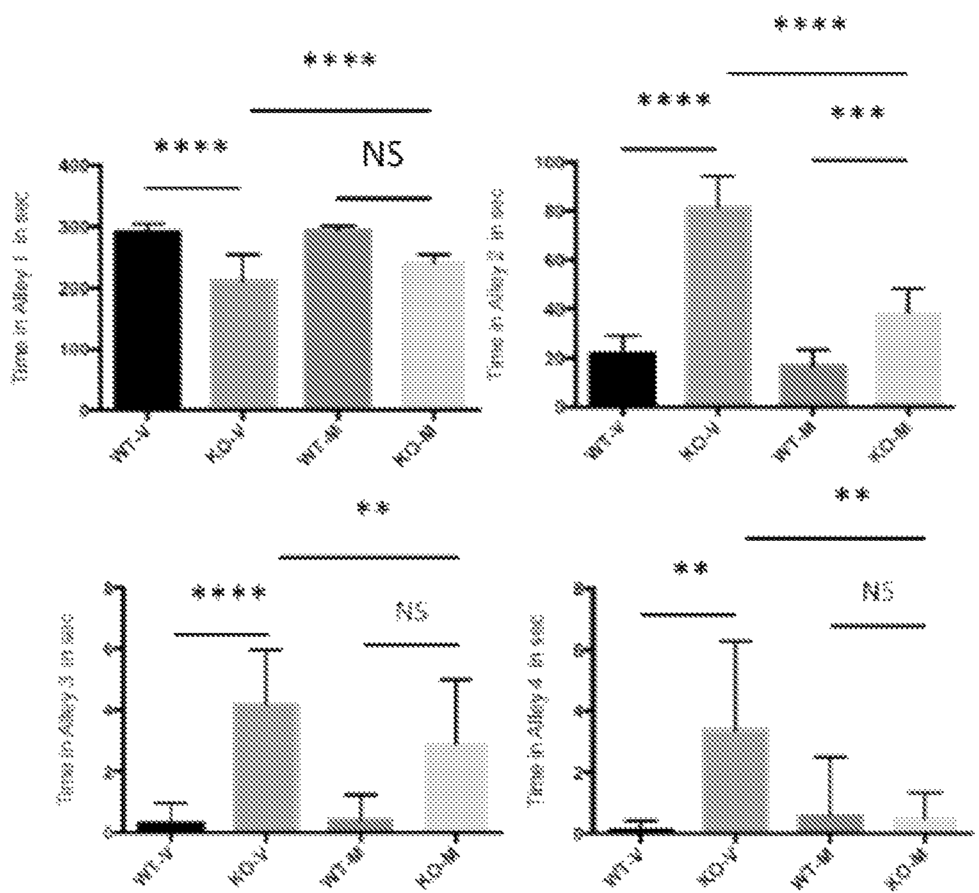
FIG. 5 shows the effect of seven days of once daily treatment with vehicle (V) or 150 mg/kg metadoxine (M) on behavior in the successive alleys task in groups of N=10 Wild Type (WT) or Fmr1 knockout (KO)2-months old mice. The successive alleys of the apparatus presented progressively more anxiogenic environments to explore mice. Movement down the alleys therefore assessed anxiety. In addition, overall activity levels could also be quantitated in the apparatus.

Successive Alleys:

The effect of seven days of once daily treatment with vehicle or 150 mg/kg metadoxine on behavior in the successive alleys task in groups of N=10 WT or Fmr1 knockout mice is shown in FIG. 5 and further described below.

The successive alleys test effectively measured anxiety (latency to enter the Alley 1) and hyperactivity (Alleys 2 to 4). Progression from Alley 1 through the successive Alleys 2, 3, and 4 was associated with exposure to an increasingly brightly colored environment with increasingly lower walls and narrower, more exposed open arms. Time spent on, and entries into, the open arms indicated anxiety; conversely, increasing time spent in more open arms reflected hyperactivity. These factors allowed for a sensitive test bracketing a range of anxiety-like behaviors together with hyperactivity.

Alley 1:

The Fmr1 knockout mice showed more anxiety than WT mice ($p<0.001$). Fmr1 knockout mice treated with metadoxine showed an amelioration in anxiety compared with the vehicle treated Fmr1 knockout mice ($p<0.001$), such that complete normalization occurred. There was no difference between the metadoxine-treated Fmr1 knockout and metadoxine-treated WT mice. Also, metadoxine treatment had no effect on WT mice.

Alley 2:

WT mice showed less activity in Alley 2 when compared with the Fmr1 knockout mice ($p<0.0001$). Treatment with metadoxine reduced hyperactivity in the Fmr1 knockout mice ($p<0.001$), although this reversal of hyperactivity was partial since metadoxine-treated Fmr1 knockout and WT mice differed ($p<0.001$). Metadoxine treatment had no effect on WT mice.

Alley 3:

Fmr1 knockout mice showed hyperactivity compared to WT mice ($p<0.0001$). This hyperactivity was not reversed by metadoxine, since metadoxine-treated Fmr1 knockout mice did not differ from vehicle-treated Fmr1 knockout mice. Metadoxine treatment had no effect on WT mice.

Alley 4:

Fmr1 knockout mice showed hyperactivity compared to WT mice ($p<0.01$). Metadoxine treatment reversed this hyperactivity since metadoxine-treated Fmr1 knockout mice showed less activity than vehicle-treated Fmr1 knockout mice ($p<0.01$). This effect reflected a normalization since metadoxine-treated Fmr1 knockout mice did not differ from metadoxine-treated WT mice. Metadoxine treatment had no effect on WT mice.

Overall, without wishing to be bound by theory, the successive alleys test showed that Fmr1 knockout mice had increased anxiety and hyperactivity compared to WT mice. Metadoxine treatment reduced this anxiety and hyperactivity in the Fmr1 knockout mice whilst leaving WT mice unaffected.

Biochemical Analyses

Figure 6:
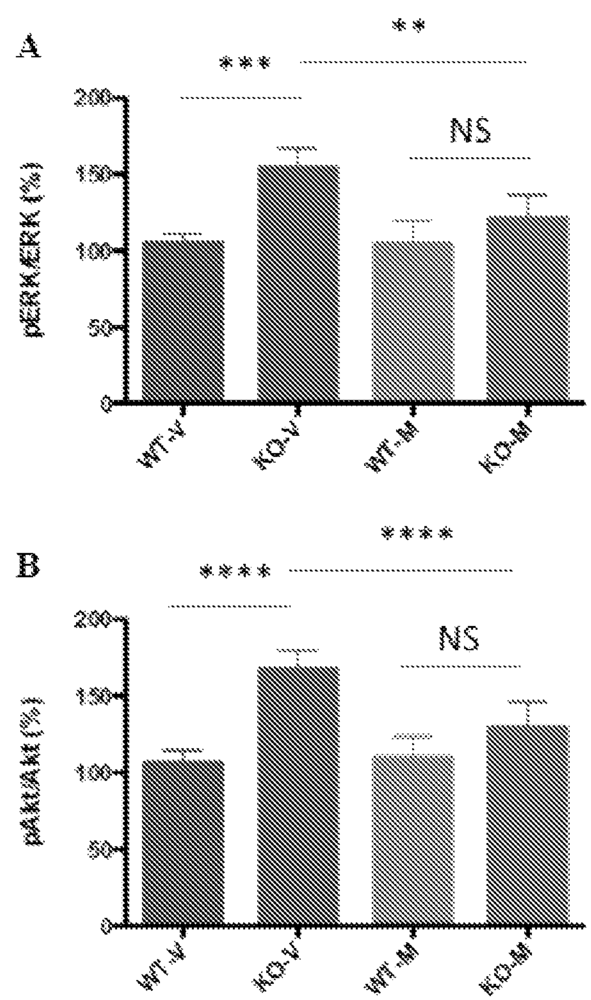
FIG. 6 shows the effect of seven days of once daily intraperitoneal administration of vehicle (V) or 150 mg/kg metadoxine (M) on whole brain levels of phosphorylation of ERK (indicative of ERK activity) (Panel A) and Akt (indicative of Akt activity) (Panel B) in 2-months Fmr1 knockout (KO) or Wild Type (WT) mice. Data shown are mean±sem. N=5 mice per group. p<0.01, *p<0.001, ****p<0.0001, and NS=Not Significant.

Phosphorylation of ERK and Akt:

The effect of seven days of once daily intraperitoneal treatment with either vehicle or 150 mg/kg metadoxine in N=5 Fmr1 knockout or WT mice on whole brain phosphorylation of ERK or Akt in the brain is shown in FIG. 6. Phosphorylation levels were assessed as the ratio of phosphorylated to total ERK. An increase in this ratio indicated activation of ERK. Phosphorylation of ERK was increased in vehicle-treated Fmr1 knockout mice compared to vehicle controls ($p<0.001$)—this effect replicated the aberrant activation of ERK seen in human subjects with Fragile X Syndrome (Wang et al., 2012). This effect was reduced by metadoxine treatment ($p<0.01$) such that there was no difference compared to metadoxine-treated WT mice. Metadoxine had no effect on phosphorylation of ERK in WT mice or total ERK levels in any mice. The ratio of phosphorylated Akt to total AKT was also increased in vehicle-treated Fmr1 knockout mice compared to vehicle-treated WT mice ($p<0.0001$). Treatment with metadoxine reduced the relative levels of phosphorylated Akt in Fmr1 knockout mice ($p<0.01$), such that Fmr1 knockout mice did not differ from the controls. Metadoxine treatment had no effect on WT mice, or on the total Akt levels of any mice.

Example 3: The Evaluation of Metadoxine in the Fmr1 Knockout Fragile X Mouse Model (Study 2)

Behavioral Effects of Metadoxine in 6 Month Old Fmr1 Knockout Mice

Figure 7:
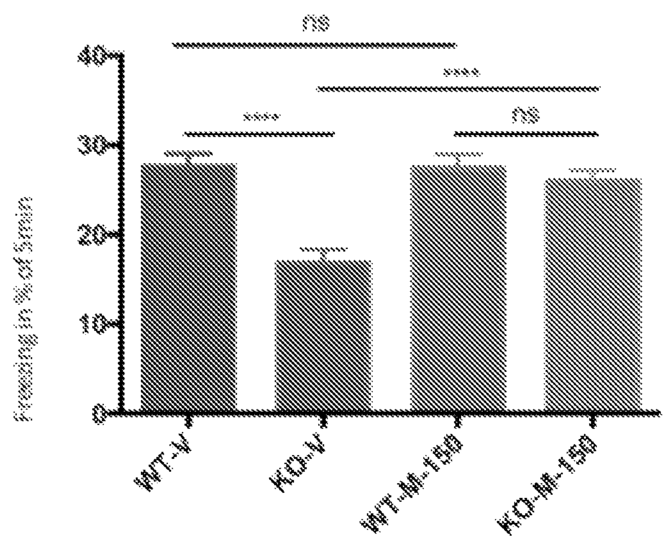
FIG. 7 shows the effect of once daily ip administration of vehicle (V) or 150 mg/kg metadoxine (M) for 7 days in 6 month old Fmr1 knockout (KO) or Wild Type (WT) mice on contextual fear conditioning. Data shown are mean±sem, N=10 mice per group. ****p<0.0001 and ns=Not Significant.

Contextual Fear Conditioning:

An initial experiment tested the effect of intraperitoneal administration of vehicle or 150 mg/kg metadoxine once daily for seven days on contextual fear conditioning in groups of N=10 WT and Fmr1 knockout mice aged six months. Vehicle-treated Fmr1 knockout mice (KO-V) showed a deficit in learning in the contextual fear conditioning paradigm when compared with vehicle-treated WT mice (WT-V) as reflected in a reduction in freezing during the test session (FIG. 7 ($p<0.0001$)). Metadoxine administration reversed the learning deficit effect in Fmr1 knockout mice ($p<0.0001$ KO-M-150 vs. KO-V). This was a complete reversal such that metadoxine-treated KO mice did not differ from metadoxine-treated WT mice.

Figure 8:
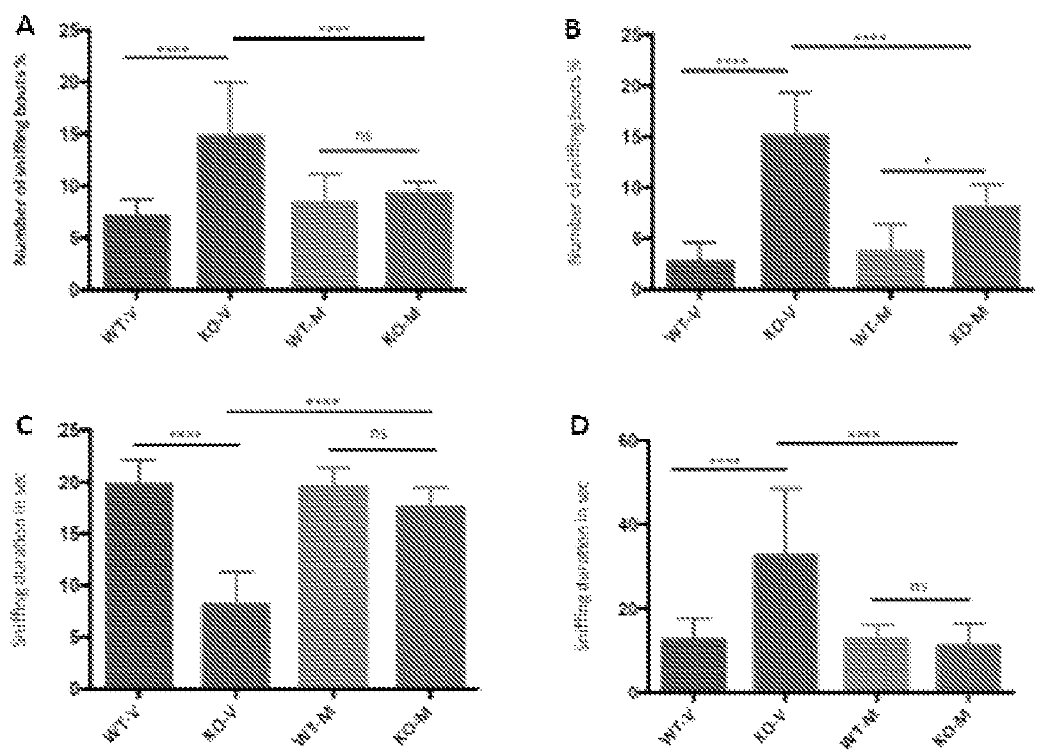
FIG. 8 shows the effect of once daily ip administration of vehicle (V) or 150 mg/kg metadoxine (M) for 7 days in 6 month old Fmr1 knockout (KO) or Wild Type (WT) mice on social approach (Panels A and C) and social memory (Panels B and D) behavior, as measured by number of sniffing bouts or duration of sniffing. Data shown are mean±sem, N=10 mice per group. *p<0.05, ****p<0.0001, and ns=Not Significant.

Social Approach and Social Memory:

Social approach data (initial Trial 1) are shown in FIG. 8. Panel A (number of sniffing bouts) and Panel C (duration of sniffing). Social memory data (Trial 2, 24 hour after Trial 1) are shown in FIG. 8, Panel B (number of sniffing bouts) and Panel D (duration of sniffing). These results are further discussed below.

During Trial 1, Fmr1 knockout mice showed an increased number of sniffing bouts ($p<0.0001$) (See FIG. 8, Panel A) and a reduced duration of sniffing ($p<0.0001$) (See FIG. 8, Panel C) compared to WT mice. These social interaction deficits are consistent with those reported by other researchers in Fmr1 knockout mice (Thomas et al., 2011). For both number of bouts and duration of sniffing, treatment with metadoxine produced reversals of abnormalities in Fmr1 knockout mice ($p<0.0001$ KO-M-150 vs. KO-V for each), such that metadoxine-treated Fmr1 knockout mice did not differ from metadoxine-treated WT mice for the number of sniffing bouts measurement. Whilst rescue was shown on the duration of sniffing measure, this effect was partial since Fmr1 knockout mice remained different compared to WT mice after metadoxine treatment ($p<0.05$). Metadoxine was without effect on WT mice. These data showed that abnormal social approach behaviors in Fmr1 knockout mice were rescued by metadoxine.

During Trial 2, Fmr1 knockout mice showed both an increase in number of sniffing bouts and an increase in duration of sniffing (p<0.0001 for each measure, FIG. 8, Panels B and D, respectively) compared to Wild Type mice. This reflected a failure of habituation and therefore, a social memory deficit. Metadoxine treatment reduced these differences (p<0.0001 for KO-M-150 vs. KO-V). The reversal for number of sniffing bouts was partial since a difference remained between metadoxine-treated Fmr1 knockout mice and metadoxine-treated WT mice (p<0.05). The reversal by metadoxine was complete for sniffing duration, since no difference was observed between metadoxine-treated Fmr1 knockout and metadoxine-treated WT mice. Metadoxine treatment was without effect on WT mice. These data showed that metadoxine reduced social memory impairments in Fmr1 knockout mice. This reduction in social memory deficit is illustrated below by a calculation of the social memory ratio (described in Example 1):

Social memory ratio was defined as the duration of sniffing bouts: trial 2/trial 1+2. Therefore, an example of no memory was (e.g. 20/(20+20)=0.5, while an example of memory was (e.g. 10/(20+10)=<0.5.

The calculated social memory ratios were as follows:

WT-*V* Trial 2/trial 1+Trial 2: 12.4/12.4+26.8=0.3, <0.5 memory

KO-*V* Trial 2/trial 1+Trial 2: 325/325+24.1=0.9,No memory

WT-*M* Trial 2/trial 1+Trial 2: 12.5/38.5+12.5=0.2, <0.5 memory

KO-*M* Trial 2/trial 1+Trial 2: 12.7/28.4+12.7=0.3, <0.5 memory

Biochemical Effects of Metadoxine in 6 Month Old Fmr1 Knockout Mice

Figure 9:
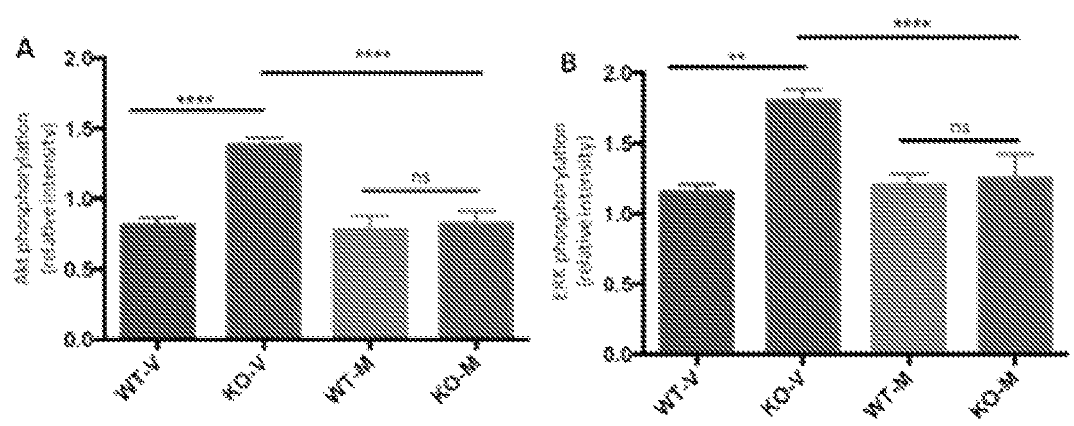
FIG. 9 shows the effect of once daily ip administration of vehicle (V) or 150 mg/kg metadoxine (M) for 7 days on whole brain levels of phosphorylation of ERK (Panel A) and Akt (Panel B) in 6 month old Fmr1 knockout (KO) or Wild Type (WT) mice. Data shown are mean±sem, N=10 mice per group. *p<0.05, p<0.01, **p<0.0001, and ns=Not Significant.

The effect of seven days of once daily ip treatment with either vehicle or 150 mg/kg metadoxine in N=10 Fmr1 knockout or WT mice on whole brain pERK (FIG. 9, Panel A) and pAkt (FIG. 9, Panel B) in the brain following the behavioral tests described above is shown in FIG. 9. Specifically, FIG. 9, Panel A shows brain levels of pAkt, which were increased in Fmr1 knockout mice compared to WT mice as seen in previous experiments (P<0.0001). Treatment with metadoxine reversed this increase in brain pAkt (p<0.0001 for KO-M-150 vs. KO-V) such that metadoxine-treated Fmr1 knockout mice did not differ from metadoxine-treated WT mice. FIG. 9, Panel B shows brain levels of pERK which were increased in Fmr1 knockout mice compared to WT mice as seen in previous experiments (p<0.0001 for KO-M-150 vs. KO-V). This increase was reversed by metadoxine treatment (p<0.0001) such that metadoxine-treated Fmr1 knockout mice did not differ from metadoxine-treated WT mice.

Figure 10:
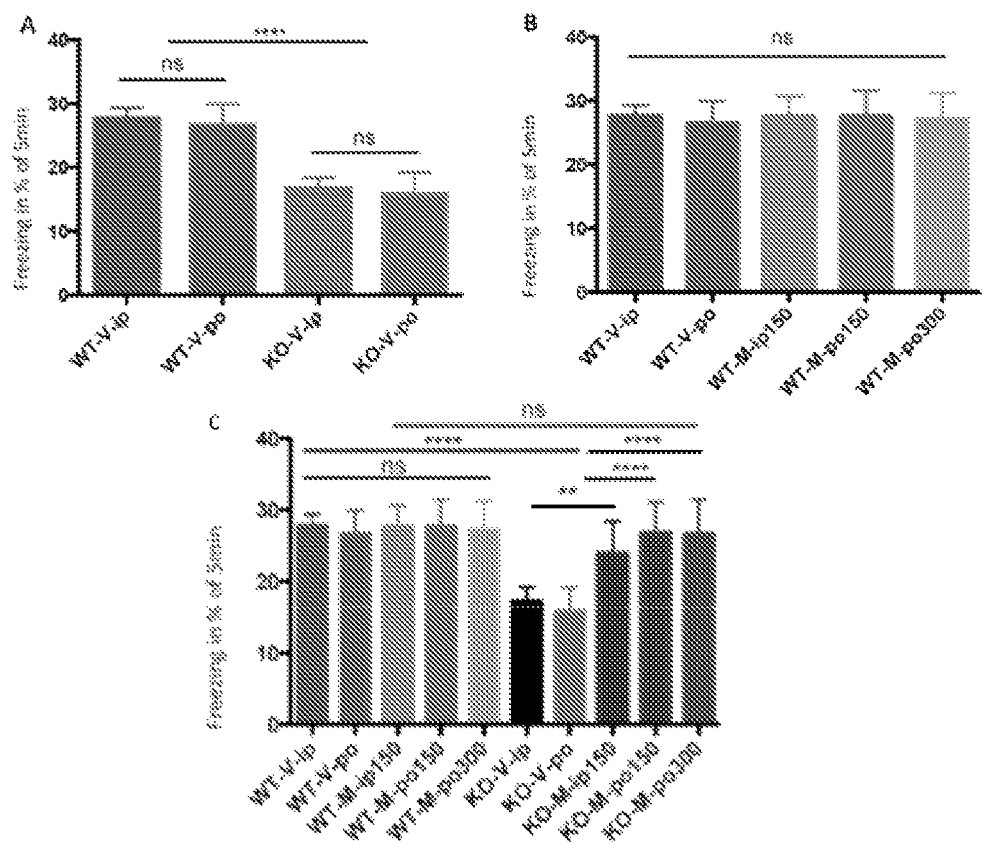
FIG. 10 shows the effect of once daily metadoxine (M) at 150 mg/kg ip or oral administration (po) of vehicle (V) or metadoxine at 150 and 300 mg/kg for 7 days on contextual fear conditioning in 2 month old Fmr1 knockout (KO) or Wild Type (WT) mice. Data shown are mean±sem, N=10 mice per group. Specifically, Panel A shows ip and oral treatment with vehicle in Fmr1 knockout and Wild Type mice. Panel B shows ip and oral treatment with metadoxine in Wild Type mice. Panel C shows ip and oral treatment with metadoxine in Fmr1 knockout mice. p<0.01, **p<0.0001, and ns=Not Significant.

Effect of Metadoxine Following Intraperitoneal or Oral Administration on the Behavior of 2 Month Old Mice FIG. 10 shows the effect of administration of once daily metadoxine at doses of 150 mg/kg ip or 150 and 300 mg/kg orally for seven days on contextual fear conditioning in two month old Fmr1 knockout and WT mice. Specifically, FIG. 10, Panel A shows contextual fear conditioning data from Fmr1 knockout and WT mice after ip and oral treatment with vehicle. There were no differences related to the route of administration of vehicle. Fmr1 knockout mice showed a reduction in freezing behavior compared to WT mice after vehicle treatment via ip and oral routes (p<0.0001 in each case). FIG. 10, Panel B shows the effect of metadoxine treatment via both routes of administration in WT mice. No effects were seen. FIG. 10, Panel C shows that ip 150 mg/kg and oral 150 and 300 mg/kg metadoxine treatment in Fmr1 knockout mice reversed the decrease in freezing behavior seen in Fmr1 knockout mice (p<0.01, p<0.0001, and p<0.0001, for KO-M-ip, KO-M-po150, and KO-M-po 300 vs. KO-V-ip and KO-V po, respectively). The effect of administration with 150 mg po metadoxine did not differ from the effect of administration of 300 mg/kg po metadoxine. The effect of 150 and 300 mg/kg oral metadoxine in Fmr1 knockout mice did not differ from the effect of 150 mg/kg ip metadoxine. In each case, the reversal was complete since metadoxine-treated Fmr1 knockout mice did not differ from metadoxine-treated WT mice.

FIG. 11 shows the effect of administration of once daily metadoxine at doses of 150 mg/kg ip or 150 and 300 mg/kg orally for seven days on social approach and social memory in Fmr1 knockout and WT mice. Specifically, FIG. 11, Panel A shows the effect of vehicle or metadoxine at 150 mg/kg ip or 150 and 300 mg/kg orally on social approach behavior in Fmr1 knockout or WT mice. After ip or oral treatment with vehicle, the duration of sniffing behavior in Fmr1 knockout mice was reduced compared to WT mice (p<0.0001 for each). Metadoxine treatment at any dose was without effect on WT mice. However, metadoxine treatment at 150 mg/kg ip, 150 mg/kg, and 300 mg/kg orally produced reversals of the social approach deficit seen in Fmr1 knockout mice (p<0.0001 for KO-M-po150 and KO-M-po300 vs. KO-V po, respectively). The effect of oral metadoxine was not dose dependent between 150 and 300 mg/kg. This reversal was complete since metadoxine-treated Fmr1 knockout mice did not differ from metadoxine-treated WT mice. The effect of 150 mg/kg ip metadoxine in Fmr1 knockout mice did not differ from the effect of 150 mg/kg oral or 300 mg/kg oral metadoxine. FIG. 11, Panel B shows the effect of vehicle or metadoxine at 150 mg/kg ip or 150 and 300 mg/kg orally on social memory in Fmr1 knockout or WT mice. After ip or oral treatment with vehicle, the duration of sniffing behavior in Fmr1 knockout mice was increased compared to WT mice (p<0.0001 for each). Metadoxine treatment at any dose was without effect on WT mice. However, metadoxine treatment at 150 mg/kg ip, 150 mg/kg orally, and 300 mg/kg orally produced reversals of the social approach deficit seen in Fmr1 knockout mice (p<0.0001, p<0.05, and p<0.01 for KO-M-ip 150, KO-M-po 150, and KO-M-po 300 vs. KO-V-ip and KO-V po, respectively). This reversal was complete since metadoxine-treated Fmr1 knockout mice did not differ from metadoxine-treated WT mice. The effect of 150 mg/kg ip metadoxine in Fmr1 knockout mice did not differ from the effect of 150 mg/kg oral or 300 mg/kg oral metadoxine. Also, there was no dose dependency for the effects of oral metadoxine treatment between 150 mg/kg and 300 mg/kg.

Effect of Metadoxine on Biochemical Markers Following Intraperitoneal or Oral Administration in 2 Month Old Mice Peripheral Lymphocytes: FIG. 12 shows the effect of administration of once daily metadoxine at doses of 150 mg/kg ip or 150 mg/kg and 300 mg/kg orally for 7 days on lymphocyte pAkt (FIG. 12. Panel A) and pERK (FIG. 12, Panel B) as determined by flow cytometry in two month old Fmr1 knockout and WT mice. Specifically, FIG. 12, Panel A shows that vehicle-treated Fmr1 knockout mice exhibited increased phosphorylation of lymphocyte Akt (p<0.0001 for both ip and oral administration) compared to WT mice receiving equivalent vehicle treatment. Treatment with once daily metadoxine at 150 mg/kg ip or oral doses of 150 mg/kg or 300 mg/kg for 7 days normalized overactivated Akt, such that pAkt levels did not differ between metadoxine-treated Fmr1 knockout mice and WT mice receiving the same treatment. FIG. 12, Panel B shows that vehicle-treated Fmr1 knockout mice showed increased phosphorylation of lymphocyte ERK ($p<0.0001$ for both ip and oral administration) compared to WT mice receiving equivalent vehicle treatment. Treatment with once daily metadoxine at 150 mg/kg ip or oral doses of 150 mg/kg or 300 mg/kg for 7 days normalized overactivated ERK such that pERK levels did not differ between metadoxine-treated Fmr1 knockout mice and WT mice receiving the same treatment.

Brain Regions:

FIG. 13 shows the effect of administration of 150 mg/kg metadoxine for seven days on pERK levels in hippocampus, pre-frontal cortex, and striatum. pERK levels were increased in Fmr1 knockout mice compared to WT mice in all three brain regions ($p<0.0001$ in all cases). pERK levels were decreased in metadoxine-treated Fmr1 knockout mice compared to vehicle-treated Fmr1 knockout mice ($p<0.0001$ in all cases). There were no differences between KO-M and WT-M groups in the hippocampus and striatum, showing complete reversal of activation of ERK. The effect in pre-frontal cortex was partial, the KO-V and KO-M groups remained different ($p<0.05$). Metadoxine was without effect on WT mice.

FIG. 14 shows the effect of administration of 150 mg/kg metadoxine for seven days on pAkt levels in hippocampus, pre-frontal cortex and striatum. pAkt levels were increased in Fmr1 knockout mice compared to WT mice in all three brain regions ($p<0.0001$ in all cases). pAkt levels were decreased in metadoxine-treated Fmr1 knockout mice compared to vehicle-treated Fmr1 knockout mice in all three brain regions ($p<0.0001$ in all cases). In all cases, there were no differences between KO-M and WT-M groups, showing complete reversal of activation of Akt. Metadoxine was without effect on WT mice. Reduction in brain and blood elevated levels of phosphorylated ERK and Akt correlated with the improved behavioral outcomes of Fmr1 knockout mice, suggesting that the phosphorylation levels are biomarkers of metadoxine treatment response Effects of Metadoxine on Dendritic Filopodia Density and Maturation in Primary Hippocampal Neurons from Fmr1 Knockout Mice In Vitro FIG. 15 (Panels A-C) shows the effect of treatment for five hours with 300 μM metadoxine. Dendrites were divided into 10 segments of 10 μm, each based on distance from the soma (proximal to distal, left to right). Spine density was increased in neurons from Fmr1 knockout mice compared to neurons from WT mice in segment 3. Specifically, FIG. 15, Panel A shows the density of neuronal filopodia. Primary hippocampal neurons from Fmr1 knockout mice displayed an increased density of filopodia ($p<0.001$). Treatment with 300 μM metadoxine reduced the aberrant increase in density of neuronal filopodia in Fmr1 knockout mice ($p<0.001$). Neurons from Fmr1 knockout mice showed filopodia with characteristics of immaturity, being longer (FIG. 15, Panel B ($p<0.01$)) and narrower (FIG. 15, Panel C ($p<0.01$)). Treatment with metadoxine reversed this increase in filopodia length (FIG. 15, Panel B ($p<0.01$)) and reversed the decrease in width (FIG. 15, Panel C ($p<0.001$)).

Effects of Metadoxine on De Novo Hippocampal Protein Synthesis in the Fmr1 Knockout Mouse In Vitro FIG. 16 shows the effect of treatment with either vehicle or 300 μM metadoxine on basal de novo protein synthesis in 400 μM hippocampal slices from Fmr1 knockout or WT mice. Protein synthesis was higher in vehicle-treated hippocampi from Fmr1 knockout mice than vehicle-treated WT control hippocampi ($p<0.0001$). Metadoxine treatment reduced protein synthesis rates in Fmr1 knockout mouse hippocampi. This effect was partial since hippocampi from Fmr1 knockout mice retained higher protein synthesis rates than metadoxine-treated hippocampi from WT mice ($p<0.001$).

TABLE 1

Summary of Effects of Metadoxine (150 mg/kg) in the Mouse Model of Fragile X Syndrome

| Test | Route/dose | Abnormal in fmr1 KO mice (Y/N) | Reduction of deficit (Y/N) | Replication of Previous Study |
|---|---|---|---|---|
| Behavioral effects in 6 month old mice | | | | |
| Contextual fear conditioning | 150 mg/kg i.p. | Deficit | Y | Y |
| Social approach | 150 mg/kg i.p. | Y | Y | Y |
| Social memory | 150 mg/kg i.p. | Y | Y | Not tested |
| Biochemical effects in 6 month old mice | | | | |
| Phosphorylation of brain Akt | 150 mg/kg i.p. | Increased in fmr1 KO mice | Y | Y |
| Phosphorylation of brain ERK | 150 mg/kg i.p. | Increased in fmr1 KO mice | Y | Y |
| Phosphorylation of brain GSK3β (tyr219/tyr279) | 150 mg/kg i.p. | Increased in fmr1 KO mice | N | Not tested |
| Brain GST levels | 150 mg/kg i.p. | Decreased in fmr1 KO mice | Y | Y |
| Behavioral effects of Metadoxine following intraperitoneal or oral administration in 2 month old mice | | | | |
| Contextual fear conditioning | 150 mg/kg ip | Y | Y | Y |
| Social approach behaviour | 150 mg/kg ip | Y | Y | Y |
| Social memory | 150 mg/kg ip | Y | Y | Not tested |
| Contextual fear conditioning | 150 mg/kg po | Y | Y | Not tested |
| Social approach behaviour | 150 mg/kg po | Y | Y | Not tested |
| Social memory | 150 mg/kg po | Y | Y | Not tested |
| Contextual fear conditioning | 300 mg/kg po | Y | Y | Not tested |
| Social approach behaviour | 300 mg/kg po | Y | Y | Not tested |
| Social memory | 300 mg/kg po | Y | Y | Not tested |
| Biochemical effects of Metadoxine following intraperitoneal or oral administration in 2 month old mice | | | | |
| Lymphocyte pAkt and pERK | 150 mg/kg ip | Increased | Y | Not tested |
| Lymphocyte pGSK3β (tyr219/tyr279) | 150 mg/kg ip | Increased | N | Not tested |

TABLE 1-continued

Summary of Effects of Metadoxine (150 mg/kg) in the Mouse Model of Fragile X Syndrome

| Test | Route/dose | Abnormal in fmr1 KO mice (Y/N) | Reduction of deficit (Y/N) | Replication of Previous Study |
|---|---|---|---|---|
| Lymphocyte GST | 150 mg/kg ip | Decreased | N | Not tested |
| Lymphocyte pAkt and pERK | 150 mg/kg po | Increased | Y | Not tested |
| Lymphocyte pGSK3β (tyr219/tyr279) | 150 mg/kg po | Increased | N | Not tested |
| Lymphocyte GST | 150 mg/kg po | Decreased | N | Not tested |
| Lymphocyte pAkt and pERK | 300 mg/kg po | Increased | Y | Not tested |
| Lymphocyte pGSK3β (tyr219/tyr279) | 300 mg/kg po | Increased | N | Not tested |
| Lymphocyte GST | 300 mg/kg po | Decreased | N | Not tested |
| Hippocampal pERK | 150 mg/kg ip | Increased | Y | Not tested |
| Prefrontal cortex pERK | 150 mg/kg ip | Increased | Y | Not tested |
| Striatum pERK | 150 mg/kg ip | Increased | Y | Not tested |
| Hippocampal pAkt | 150 mg/kg ip | Increased | Y | Not tested |
| Prefrontal cortex pAkt | 150 mg/kg ip | Increased | Y | Not tested |
| Striatum pAkt | 150 mg/kg ip | Increased | Y | Not tested |
| Hippocampal pGSK3β (ser9) | 150 mg/kg ip | Normal levels | NA | Not tested |
| Prefrontal cortex pGSK3β (ser9) | 150 mg/kg ip | Decreased | N | Not tested |
| Striatum pGSK3β (ser9) | 150 mg/kg ip | Decreased | Y | Not tested |
| Hippocampal GST | 150 mg/kg ip | Decreased | N | Not tested |
| Prefrontal cortex GST | 150 mg/kg ip | Decreased | N | Not tested |
| Striatum GST | 150 mg/kg ip | Decreased | Y | Not tested |
| Hippocampal pS6K1 (ser235/236) | 150 mg/kg ip | Increased | N | Not tested |
| Prefrontal cortex pS6K1 (ser235/236) | 150 mg/kg ip | Increased | N | Not tested |
| Striatum pS6K1 (ser235/236) | 150 mg/kg ip | Increased | N | Not tested |
| Hippocampal pS6K1 (ser240/244) | 150 mg/kg ip | Increased | N | Not tested |
| Prefrontal cortex pS6K1 (ser240/244) | 150 mg/kg ip | Increased | N | Not tested |
| Striatum pS6K1 (ser240/244) | 150 mg/kg ip | Increased | N | Not tested |
| Effects of Metadoxine on filopodia density and maturation in neurons from fmr1 knockout mice in vitro | | | | |
| Neuronal filopodia density | 300 μM | Increased | Y | Not tested |
| Neuronal filopodia length | 300 μM | Increased | Y | Not tested |
| Neuronal filopodia width | 300 μM | Decreased | Y | Not tested |
| Effects of Metadoxine on de novo hippocampal protein synthesis in fmr1 knockout mice in vitro | | | | |
| De novo hippocampal protein synthesis rate | 300 μM | Increased | Y | Not tested |

We claim:

1. A method of assessing the effectiveness of a metadoxine treatment regimen in a subject having Fragile X Syndrome who has received metadoxine treatment, the method comprising:

a) measuring the amount of phosphorylated ERK and Akt protein in a sample derived from the subject, wherein the sample is whole blood or a fraction thereof;

b) measuring the total amount of ERK and Akt protein in the sample;

c) calculating a ratio of the amount of phosphorylated ERK and Akt protein determined in step (a) to the amount of ERK and Akt protein determined in step b); and d) comparing the calculated ratio of step c) to a calculated ratio measured from a non-diseased subject, wherein when the calculated ratio of step c) is similar to the calculated ratio of the non-diseased subject, indicates that the treatment is effective.

2. A method of diagnosing a subject with Fragile X Syndrome as a responder to a metadoxine treatment regimen and treating Fragile X syndrome in the subject, the method comprising:

a) measuring the amount of phosphorylated ERK and Akt protein in a sample derived from the subject, wherein the sample is whole blood or a fraction thereof;

b) measuring the total amount of ERK and Akt protein in the sample;

c) calculating a ratio of the amount of phosphorylated ERK and Akt protein determined in step (a) to the amount of ERK and Akt protein determined in step b);

d) comparing the calculated ratio of step c) to a calculated ratio measured from a non-diseased subject and diagnosing the subject with Fragile X Syndrome as a responder to a metadoxine treatment regimen when the calculated ratio of step c) is higher than the calculated ratio of the non-diseased subject; and e) administering a metadoxine treatment regimen to the diagnosed subject.

3. A method of monitoring a metadoxine treatment regimen in a subject having Fragile X Syndrome, the method comprising:

a) measuring the amount of phosphorylated ERK and Akt protein in a first sample from the subject at a first period of time, wherein the first sample is whole blood or a fraction thereof;

b) measuring the total amount of ERK and Akt protein in the first sample at the first period of time;

c) calculating a first ratio of the amount of phosphorylated ERK and Akt protein determined in step a) to the amount of total ERK and Akt protein determined in step b);

d) measuring the amount of phosphorylated ERK and Akt protein in a second sample from the subject at a second period of time, wherein the second sample is whole blood or a fraction thereof;

e) measuring the total amount of ERK and Akt protein in the second sample at the second period of time;

f) calculating a second ratio of the amount of phosphorylated ERK and Akt protein determined in step d) to the total amount of ERK and Akt protein determined in step e) to produce a second ratio;

g) comparing the first ratio to the second ratio.

4. The method of claim 3, wherein when the second ratio is lower than the first ratio, indicates that the treatment is effective.

5. The method of any one of claims 1-3, wherein the measuring steps comprise an immunoassay.

6. The method of any one of claims 1-3, wherein the sample is a peripheral blood mononucleated cell (PBMC).

7. The method of claim 6, wherein the PBMC is a lymphocyte or a monocyte.

* * * * *